(12) United States Patent
Eyal et al.

(10) Patent No.: US 7,238,837 B1
(45) Date of Patent: Jul. 3, 2007

(54) PROCESS FOR THE RECOVERY OF LACTIC ACID FROM AQUEOUS LACTATE SALT SOLUTIONS, INVOLVING THE USE OF ION EXCHANGERS

(76) Inventors: Aharon Meir Eyal, 32 Baitar Street, 93380 Jerusalem (IL); Ponnampalam Elankovan, 2365 Club Meridian Dr., Okemos, MI (US) 48864

( * ) Notice: Subject to any disclaimer, the term of this patent is extended or adjusted under 35 U.S.C. 154(b) by 0 days.

(21) Appl. No.: 09/147,914

(22) PCT Filed: Oct. 2, 1997

(86) PCT No.: PCT/US97/17774

§ 371 (c)(1),
(2), (4) Date: May 25, 1999

(87) PCT Pub. No.: WO98/15518

PCT Pub. Date: Apr. 16, 1998

(30) Foreign Application Priority Data

Oct. 9, 1996 (IL) .................................... 119389

(51) Int. Cl.
*C07C 59/08* (2006.01)
*C07C 51/42* (2006.01)

(52) U.S. Cl. ...................... 562/589; 562/580
(58) Field of Classification Search .............. 562/580, 562/589

See application file for complete search history.

(56) References Cited

U.S. PATENT DOCUMENTS

| | | | | |
|---|---|---|---|---|
| 3,202,705 | A | * | 8/1965 | Powell et al. ............... 562/580 |
| 4,358,464 | A | | 11/1982 | Soehnlen ...................... 426/41 |
| 4,444,881 | A | * | 4/1984 | Urbas ......................... 435/139 |
| 4,467,034 | A | * | 8/1984 | Voelskow et al. ........... 435/139 |
| 5,210,296 | A | * | 5/1993 | Cockrem et al. ............ 562/589 |
| 5,252,473 | A | * | 10/1993 | Walkup et al. ............... 435/135 |
| 5,369,122 | A | | 11/1994 | Steinmetzer ................. 514/423 |
| 5,453,365 | A | * | 9/1995 | Sterzel et al. ................ 435/135 |
| 5,510,526 | A | * | 4/1996 | Baniel et al. ................ 562/580 |
| 5,766,439 | A | * | 6/1998 | Eyal et al. .................... 204/524 |

FOREIGN PATENT DOCUMENTS

| | | | |
|---|---|---|---|
| EP | 0614983 A | * | 3/1994 |
| EP | 0393818 A | * | 9/1994 |
| EP | 95/32301 | * | 11/1995 |
| FR | 2674848 | | 10/1992 |
| JP | 00917881 | | 4/1989 |
| WO | 9419307 | | 9/1994 |
| WO | 9711047 | | 3/1997 |

OTHER PUBLICATIONS

Patent Abstracts of Japan, vol. 13, No. 302 (C-616) of JP 01091788 dated Apr. 11, 1989.

* cited by examiner

*Primary Examiner*—Taylor Victor Oh
(74) *Attorney, Agent, or Firm*—Ladas & Parry LLP

(57) ABSTRACT

The invention provides a process for the recovery of lactic acid from aqueous solutions containing at least one water-soluble lactate salt and having a pH of about between 4 and 14, comprising the steps of: contacting said aqueous solution with a cation exchanger which is at least partially in its acid form, said cation exchanger being water immiscible in both acid and salt form, whereby ion exchange is effected, protons are transferred from the cation exchanger to the aqueous solution to acidulate it and to form lactic acid therein and cations from the aqueous solution are bound by the cation exchanger; reacting the cations carrying cation exchanger to convert it into a cation exchanger which is at least partially in its acid form and to a second product, which second product is basic and comprises the cation of the salt; and recovering lactic acid from the lactic acid-containing acidulated aqueous solution by methods known per se.

32 Claims, No Drawings

PROCESS FOR THE RECOVERY OF LACTIC ACID FROM AQUEOUS LACTATE SALT SOLUTIONS, INVOLVING THE USE OF ION EXCHANGERS

The present invention relates to a process for the recovery of lactic acid.

More particularly, the present invention relates to a process for the recovery of lactic acid from aqueous solutions containing at least one water-soluble lactate salt and having a pH of about between 4 and 14.

Lactic acid has long been used as a food additive and in various chemical and pharmaceutical applications. More recently, lactic acid has been used in the making of biodegradable polylactic acid polymers as a replacement for present plastic materials, as well as for various new uses where biodegradability is need or desired. Accordingly, there is an ever-increasing demand for lactic acid. The present invention aims at meeting this demand by providing an efficient and environmentally friendly process for producing lactic acid which avoids the consumption of bases and acids and substantially reduces, if not eliminates, the formation of waste or byproduct salts.

The production of lactic acid is commonly carried out by fermentation of a strain of the bacterial genus *lactobacillus delbrueckii* or *Lactobacillus acidophilus*. In general, the production of lactic acid by fermentation in a fermentation broth is well known in the art. The fermentation substrate consists of carbohydrates together with suitable mineral and proteinaceous nutrients. Because the lactic acid-producing microorganisms are inhibited in a strongly acidic environment, lactic acid fermentation is conducted at about neutral pH and a neutralizing agent is added for pH adjustment. As the pKa of lactic acid is 3.86, at the pH of fermentation, practically only lactate salts exist. Thus, recovery of lactic acid (in an acid form) from the fermentation liquor requires chemical conversion. Several processes were developed for such conversion.

In some of the processes the conversion liberates lactic acid in solution, e.g. by displacement with a strong acid. Thus, when calcium bases are used as the neutralizing agents in the fermentation, calcium lactate is formed. Reacting the calcium lactate-containing fermentation liquor with sulfuric acid results in precipitation of gypsum and liberation of lactic acid in the solution.

Nakanishi and Tsuda (JP 46/30176) consider production of 1-buyl lactate by extraction of an acidified crude fermentation broth with 1-butanol, followed by esterification of the extract phase. BASF (EP-0159 585) considers a similar process with isobutanol to form isobutyl lactate. The process of WO 93/00440, assigned to DU PONT, comprises the steps of: (1) simultaneously mixing a strong acid, an alcohol, and a concentrated fermentation broth which contains mainly basic salts of lactic acid, which react to form a crystal precipitate comprising basic salts of the strong acid and an impure lactate ester of the alcohol; (2) removing water from the mixture as a water/alcohol azeotrop which can be accomplished either sequentially or substantially simultaneously with step (1); removing the crystal precipitate from the mixture; and (4) distilling the impure lactate ester to remove impurities, and recovering the high purity ester.

Alternatively to purifying the lactic acid, which is liberated by displacement with a strong acid, through esterification and distillation of the ester, one could purify it by extraction. The extractant could be a relatively weak one and would allow the recovery of the extracted HLa at high concentration by back-extraction. The known (and food approved) weak extractants to be considered are amine-based ones or solvating extractants (one may consider esters, ethers, ketones, aldehydes, etc., but alkanols seem preferable).

Out of these two groups, the amine-based ones are more attractive for several reasons: (I) they are more selective and would therefore provide for higher product purity, (ii) their extraction capacity is higher and therefore the extractant flow will be lower, and (iii) the amine-based extractants show the temperature sensitivity of the extraction and therefore provide for the "uphill pumping" through back-extraction, at a temperature which is higher than that of the extraction.

These preferred amine-based extractants would not work in a simple process, where the (stronger than lactic) displacing acid is added to the lactate salt-containing solution and the liberated HLa is directly extracted by contact with the extractant. The amine-based extractant prefers the stronger acid in a mixture and would therefore reverse the reaction (remove the added acid).

Acidulating neutral fermentation liquors by the addition of acids usually results in the formation of by-product salts such as the gypsum ammonium and sodium sulfate. Reagents are consumed and disposal of undesired by-products is required.

Efforts have recently been made to recover lactic acid from fermentation liquors without the formation of such by-products. (Such processes will be referred to in the following as salt splitting processes.) In some recently published patents, liquid liquid extraction (LLE) is applied for salt splitting. Thus, in King's U.S. Pat. No. 5,132,456, a strongly basic extractant extracts part of the lactic acid from the neutral solution, which results in a lactic acid loaded extractant and a basic solution. This basic solution, which still contains most of the lactic acid values, could be recycled as a neutralizing medium to the fermentation. In Baniel's U.S. Pat. No. 5,510,526, the extraction of the acid is conducted under $CO_2$ pressure so that a bicarbonate is formed. The latter can be used as a neutralizing agent in the fermentation. In order to limit the $CO_2$ pressure to an economic one and still achieve high yields, the extractant used should be quite strong. Recovery of the extracted lactic acid from such strong extractants is difficult, as they hold strongly to it. Recovery of the extracted acid by washing with an aqueous solution of a base is feasible, but forms the lactate salt of the base. It is therefore not practical in those cases where lactic acid is the desired product. Back-extraction with water forms an overly diluted product.

U.S. Pat. No. 5,132,456 suggests a way for recovering extracted carboxylic acid from a strong extractant. It comprises leaching or back-extraction with an aqueous solution of ammonia or low molecular weight alkyl amine, especially trimethyl amine (TMA). The resultant aqueous ammonium or alkylammonium carboxylate solution can be concentrated, if necessary, and the carboxylate can be decomposed thermally to yield the product carboxylic acid and ammonia or amine which can be condensed and recycled. This process is costly and complex. According to the invention, it is particularly problematic for recovery of extracted lactic acid: "For lactic acid the decomposition is incomplete, being stopped by the formation of a viscous, almost glassy mass containing polymerized lactic acid along with substantial TMA and water. There are, however, effective ways of driving the decomposition to completion for lactic acid, such as diluting the viscous mass with an appropriate solvent (e.g. methyl isobutyl ketone) and continuing the heating and decomposition process."

With these state of the art in mind there is now provided, according to the present invention a process for the recovery of lactic acid from aqueous solutions containing at least one water-soluble lactate salt and having a pH of about between 4 and 14, comprising the steps of: (a) contacting said aqueous solution with a cation exchanger which is protonated, that is at least partially in its acid form, said cation exchanger being water immiscible in both acid and salt form, whereby ion exchange is effected, protons are transferred from said cation exchanger to the aqueous solution to acidulate it and to form lactic acid therein and cations from said aqueous solution are bound by said cation therein and cations from said aqueous solution are bound by said cation exchanger; said cations being derived from said lactate salt, (b) regenerating said cations carrying cation exchanger to convert it into a cation exchanger which is at least partially in its acid form and to a second product is a basic form of the cation of said salt; and (c) recovering lactic acid from said lactic acid-containing acidulated aqueous solution by methods known per se.

As will be realized in accordance with the present invention, said cation exchanger can be a liquid or solid cation exchanger.

Thus, on contacting the lactate salt-containing solution with the cation exchanger in its acid form an ion exchange is effected. Protons from the cation exchanger transfer into the aqueous solution where they bind with the lactate anions to form lactic acid. The cations of the lactate salt transfer at the same time to the cation exchanger and transform it into its salt form.

Solid cation exchangers carrying functional groups such as carboxyl or sulfone of the kind used, for example, for de-ionizing solutions, are suitable for the process. So are water-immiscible extractants such as fatty acids, alpha- or beta-halo carboxylic acids, sulfonic acids and mono- or di-esters of phosphoric acid. The cation exchanger salts formed are water immiscible as well, so that, unlike in the case of acidulating by a mineral acid, no salt is added to the broth. The cation exchanger in the acid form needs to be regenerated and is therefore preferably of a weak to medium acidity. It was found that in certain cases highly efficient acidulation is achievable by use of cation exchangers which are significantly weaker acids than lactic acid.

The acid/base properties of water soluble acids or bases are easily determined by their degree of dissociation in aqueous solution. The acid/base properties of water immiscible compounds are determined indirectly through their interaction with solutes in an aqueous solution. Thus the apparent acidity of various liquid or solid cation exchangers can be compared by contacting them with aqueous solutions of NaCl and determining the pH of the aqueous solution in equilibrium. The lower the pH, the stronger the apparent acidity of the cation exchanger. For comparing cation exchangers of relatively low acidity, equilibration with base solutions is preferred. Analogously, the basicity of water immiscible anion exchangers is determined by equilibration with aqueous solutions of salts or acids. Unlike in the case of water soluble acids and bases, the apparent acid/base properties found for water immiscible compounds are determined in addition to the intrinsic properties of the anion/cation exchanger, by the method of measurement, by phenomena such as steric hindrance, and by the medium (in the case of liquid exchangers).

The salt form of the water-immiscible cation exchanger can readily be treated to convert it back to its acid form. This can be achieved by contact with a solution of an acid or an acidic salt, preferably one that is stronger than the cation exchanger. Operating this way consumes a strong acid and could therefore be considered as an indirect acidulation of the lactate salt via a water immiscible cation exchanger. Unlike in the case of direct acidulation by adding a water soluble acid, no salt is formed in the aqueous solution in the case of indirect acidulation and one an use the preferred amine base extractants for the recovery of the liberated acid. Yet an acid is consumed and a by-product salt is formed. There are various ways to split this by-product salt. For example, an acidic ammonium salt of a di- or triprotic acid, e.g., $NH_4HSO_4$, could be used as the regenerant of the cation exchanger in an ammonium form. The resulting neutralized salt, namely ammonium sulfate, decomposes thermally to ammonia to be reused, and to ammonium bisulfate, which is the acidic salt, the acidulant. As long as the lactate is an ammonium lactate the regenerant could be $NaHSO_4$ or any other acidic sulfate salt, $MHSO_4$, which is easy to work with. An alkali metal M that forms $MNH_4SO_4$ of relatively low solubility is preferable, as it lowers the energy costs related to water evaporation during the thermal decomposition of the salt.

In a preferred embodiment the salt of the cation exchanger is decomposed to reform the acid form and a second product which is a basic form of said cation of said lactate salt. An example is the case where the lactate salt is ammonium lactate and an ammonium salt of the water immiscible cation exchanger is formed. The latter can be decomposed thermally to the cation exchanger in its acid form and to ammonia. Conducting the thermal decomposition at subatmospheric conditions or by transfer of a carrier gas helps in shifting the reaction in the desired direction. Steam and $CO_2$ are among the suitable carrier gases. Compared to the possibility of decomposition of a salt formed on regenerating of the acid form of the cation exchanger by an aqueous solution of an acid, direct decomposition saves on energy consumption for water evaporation. In addition, for a liquid cation exchanger, the decomposition can be assisted by changing the medium/solvent of the salt prior to its decomposition. An alternative to distillation of the second product is the precipitation thereof. Thus, thermal hydrolysis of calcium salts of the cation exchanger forms calcium hydroxide, or if conducted in the presence of $CO_2$, $CaCO_3$. The crystallization energy of these compounds assists the salt decomposition.

In a further preferred embodiment the second product is basic and can be reused as a neutralizing agent in fermentation. Thus, the lactate salt-containing aqueous solution could be a fermentation broth after removal of the biomass and possibly also after some additional pretreatments. Alternatively, it could be a stream obtained on recovery of lactic acid from broth treated by other methods. If ammonia is used for pH adjustment in the fermentation (i.e. used as the neutralizing agent there), the lactate salt in the broth will be primarily ammonium lactate. Acidulation by water immiscible cation exchanger would convert the latter from its acid form to its ammonium salt. Thermal decomposition of that ammonium salt reforms the cation exchanger in its acid form and forms a second product, ammonia which is a basic form of the ammonium cation of ammonium lactate. In fact the neutralizing agent is regenerated and can be reused in the fermentation. Thereby, the process avoids the consumption of stoichiometric amounts of a neutralizing base and of an acidulant and the formation of a stoichiometric amount of a by-product salt. Examples for other basic, second decomposition products suitable for reuse in adjusting the pH in fermentation are calcium hydroxide or carbonate and sodium hydroxide, bicarbonate or carbonate resulting from applying the process to calcium lactate or sodium lactate-containing solutions respectively.

The lactic acid in the aqueous phase resulting from the acidulation by the water immiscible cation exchanger is mostly in its free, non-dissociated form. The aqueous solution still comprises most of the impurities it had prior to the acidulation and purification of the lactic acid may be required. That can be effected by one of the very well known methods for purifying lactic acid, including distilling the acid or an ester thereof, adsorption on a solid anion exchanger and solvent extraction. Suitable extractants are solvents such as alkanols, esters, ketones, etc., or extractants comprising water immiscible amines as the main active components. The latter are also considered liquid anion exchangers. Out of these two groups, the amine-based ones are more attractive for several reasons: (i) they are more selective and would therefore provide for higher product purity, (ii) their extraction capacity is higher and therefore the extractant flow will be lower, and (iii) the amine-based extractants show the temperature sensitivity of the extraction and therefore provide for the "uphill pumping" through back-extraction at a temperature which is higher than that of the extraction.

Suitable amines are primary, secondary or tertiary amines with a total carbon atom number of at least 18. Their concentration in the extractant is preferably above 0.5 mole/Kg and more preferably between 0.7 and 1.5 mole/Kg. The upper limit is determined by the viscosity and therefore dependent on the lactic acid concentration in the lactic acid-loaded extractant (extract) and on the temperature. The diluent for the amine can comprise a variety of solvents such as kerosene, esters, ketones, aldehydes, ethers, alkanols, etc. Polar solvents enhance the extraction efficiency of the extractant due to their effect on the apparent basicity (and are therefore referred to as enhancers). The apparent basicity of the extractant can be increased by 1 to 2 pKa units by adding a suitable enhancer in an amount equivalent to more than 1 mole of enhancer to 1 mole of the amine in the extractant.

Unlike in the cases of salt splitting according to U.S. Pat. No. 5,132,456, U.S. Pat. No. 5,510,526 and others, where no acidulant is added, or where the acidulant is, in fact, a very weak acid, $CO_2$, the extractant or the anion exchanger in the present invention can be a relatively weak one. Weaker extractants or anion exchangers provide for easier recovery of the separated lactic acid. That is particularly important when the lactic acid is recovered from the extractant or from the water immiscible anion exchanger by back-extraction or by desorption with water. The weaker the extractant or the anion exchanger, the more concentrated will the aqueous product of the back-extraction (back-extract) or desorption (eluate) be. Thus, in the case of extraction by an amine-based extractant, tertiary amines are preferred over primary and secondary amines, and the enhancer content is preferably relatively low. The preferred apparent basicity of the extractant or the anion exchanger is less than 6 and more preferably less than 4.5. Alternatively, in an amine-based extractant the enhancer content in the extraction step is quite high so that the apparent basicity is higher and some of the enhancer is removed from the extract prior to the back-extraction.

Recovery of the lactic acid can be effected after the acidulation and possibly also after the separation of the water immiscible cation exchanger. Alternatively, the recovery of the lactic acid is conducted simultaneously with the acidulation so that both the water immiscible cation exchanger in its acid form and the water immiscible anion exchanger in its free base form are contacted with the lactic acid-containing solution. There are several known arrangements that allow such simultaneous contacting. In one of them the contact is effected in a unit which comprises at least two compartments. In one compartment a liquid cation exchanger is mixed with the lactate salt-containing aqueous solution, while the liquid anion exchanger is situated in or flowing through the other compartment. The two compartments are separated by a membrane that blocks transport of organic phase through it. There is no need to block water or cations. The membrane should let lactic acid through. Most anion exchange membranes and dense neutral hydrophilic membranes are suitable.

Alternatively, one compartment comprises a liquid cation exchanger and the other comprises a mixture of the lactate salt solution and a liquid anion exchanger. In that case the membrane between the compartments could be a cation exchange membrane or a dense neutral hydrophilic one. In a third option there are at least three compartments through which three streams are flowing: (I) the liquid cation exchanger, (ii) the lactate salt-containing aqueous solution, and (iii) the liquid anion exchanger. (I) and (ii) are separated by a cation exchange membrane or a dense neutral hydrophilic membrane, while (ii) and (iii) are separated by an anion exchange membrane (of the type that blocks cations, but allows protons through), or a dense neutral hydrophilic membrane. In some of these embodiments a solid cation exchanger could replace the liquid cation exchanger and/or a solid anion exchanger can replace the liquid anion exchanger.

Alternatively to a simultaneous contact with both the cation exchanger and the anion exchanger, the lactate salt-containing solution could be recycled between the two. Thus, it can be contacted with the cation exchanger for partial acidulation, then contacted with the anion exchanger for recovery of some of the free acid, then recycled to the contact with the cation exchanger and so on.

Operating the acidulation by the cation exchanger separately from the recovery of the lactic acid results in a build-up of lactic acid in the aqueous solution. This build-up hinders further acidulation, and in order to reach a nearly complete acidulation, the acidity or the cation exchanger should be similar to or higher than that of lactic acid. Simultaneous contact with, or recycle between, a cation exchanger and an anion exchanger provides for removal of the lactic acid formed on the acidulation and thereby avoids the build-up of the acid in the aqueous solution. As a result, one can use a cation exchanger with a low apparent acidity, lower than that of lactic acid. In this case the decomposition of the salt form of the cation exchanger into the cation exchanger in the acid form and a second basic product is easier.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Aqueous solutions containing 30% ammonium lactate (initial pH=5.85) are equilibrated at ambient temperature with di-(2-ethyl hexyl) phosphoric acid (DEHPA) at various organic to aqueous ratios. The pH values of the resulting aqueous phase are determined: they are 4.9, 4.1 and 3.2 for organic to aqueous wt/wt ratios of 0.5;1, 1:1 and 3:1 respectively.

In a similar experiment 30% ammonium lactate solutions are contacted with dinonyl naphthalene sulfonic acid (obtained from King Industries as 50% solution in Norpar 12). The pH of the aqueous solutions in equilibrium are 5.1 and 4.5 for organic to aqueous wt/wt ratios of 0.5:1 and 1:1 respectively.

Lowering the pH in contact with the water immiscible cation exchangers is a result of removing ammonium cations from the solution through binding to the cation exchangers and thereby forming lactic acid in said aqueous solution.

EXAMPLE 2

12.0 g aqueous solution containing 0.49 mol/Kg sodium lactate (total of 5.9 mmol lactate) is contacted in a beaker with 1.09 g dry cation exchanger Dowex 50x in its acid form (cation exchange capacity of 4.6 equivalent per gram dry). After shaking at ambient temperature for 2 hours, the solution was separated and analyzed for lactic acid by titration. 3.3 equivalents were found indicating conversion of 56% of the sodium lactate to lactic acid through cation exchange.

EXAMPLE 3

18.8 aqueous solution containing 2.4 mol/Kg ammonium lactate is equilibrated with 32.6 g DEHPA at ambient temperature. An aqueous solution containing 0.97 mol/Kg lactic acid and ammonia containing organic phase are obtained. The organic phase is heated for 2 hours while nitrogen is bubbled through it. Most of its cation exchange capacity is thereby restored. Ammonia is condensed from the vapor phase. 12.3 g of the lactic acid containing aqueous phase is equilibrated at ambient temperature with 47 g extractant containing 48 wt % tricaprylyl amine (Henkel's Alamine 336), 30% octanol and 22% kerosene. 97% of the lactic acid values in the aqueous phase are extracted into the organic phase. Back-extraction with water at 140° C. transfers more than 90% of the extracted acid into the obtained aqueous solution.

EXAMPLE 4

The following experiment tested simultaneous contacting of the lactic acid salt-containing aqueous solution with a liquid cation exchanger and a liquid anion exchanger. A three-compartment unit was used. Through one of the compartments a liquid cation exchanger was transferred. This compartment was separated by a membrane from the middle compartment, through which an aqueous solution of lactate salt was flowing. This compartment was separated by a second membrane from a third compartment through which a liquid anion exchanger was transferred. The volumes of the compartments were 10, 5 and 10 ml, respectively. The volumes of all three solutions flowing between their compartments and reservoirs were 100 ml. The flow rates for all three solutions were 50 ml/min. The membranes' working areas were $10^2$ cm.

The cation exchanger used was 1.2 mol/kg solution of DEHPA in kerosene. The anion exchanger was a solution containing 1.2 mol/kg Alamine 336+20% octanol in kerosene. The aqueous solutions were of 1.0 mol/kg sodium or ammonium lactate. The membranes situated between the cation exchanger and the aqueous solution were Neosepta CM-1 or CM-2 cation exchange membranes obtained from Tokayama Soda Co. Those situated between the aqueous solution and the anion exchanger were Neosepta ACH-45 or Neosepta AFX, both are anion exchange membranes obtained from Tokayama Soda Co, or Celgard 3400, a dense hydrophilic membrane obtained from Celanese Co.

The rates of cations transport into the cation exchanger and of the simultaneous transport of lactic acid into the anion exchanger were followed. The flow rates in all the combinations tested were typically higher than $3 \cdot 10^{-5}$ mol/m$^2$ sec.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the recovery of lactic acid from an aqueous solution containing a water-soluble lactate salt and having a pH between 4 and 14, which process comprises:
    (a) contacting said aqueous solution with a protonated cation exchanger to form an aqueous solution of lactic acid and a cation exchanger having cations bound thereto, said cations being derived from said lactate salt;
    (b) regenerating said protonated cation exchanger by treating the protonated cation exchanger with a regenerant consisting of an acid or an acidic salt solution to yield a second product, wherein said second product is a basic form of said cation of said lactate salt; and
    (c) recovering lactic acid from said aqueous solution of lactic acid.

2. The process of claim 1, wherein said recovery of lactic acid occurs simultaneously with said formation of said aqueous solution of lactic acid in step (a).

3. The process according to claim 1, wherein said regenerating step comprises heating said cation exchanger having cations bound thereto.

4. A process for the recovery of lactic acid from an aqueous solution containing a water-soluble lactate salt and having a pH between 4 and 14, which process comprises:
    (a) contacting said aqueous solution with a protonated cation exchanger to form an aqueous solution of lactic acid and a cation exchanger having cations bound thereto, said cations being derived from said lactate salt;
    (b) contacting said cation exchanger having cations bound thereto with an acidic salt of a di-or triprotic acid to regenerate said protonated cation exchanger and to neutralize the acidic salt, said neutralized salt containing a cation derived from said lactate salt and an anion of said neutralized acidic salt of a di- or triprotic acid;

(c) heating said neutralized salt to yield a second product, wherein said second product is a basic form of said cation of said lactate salt, and to regenerate said acidic salt of said di- or triprotic acid; and (d) recovering lactic acid from said aqueous solution of lactic acid.

5. The process according to claim 4, wherein said acidic salt of a di- or triprotic acid is an acidic sulfate salt having the formula $NH_4HSO_4$ or $MHSO_4$ where M is an alkali cation.

6. The process according to claim 5, wherein said acidic sulfate salt has the formula $NH_4HSO_4$ or $NaHSO_4$.

7. The process according to claim 1 or 4, wherein said cation exchanger is a water-immiscible liquid cation exchanger.

8. The process according to claim 1 or 4, wherein said cation exchanger is a solid cation exchanger.

9. The process according to claim 1 or 4, wherein said second product is used as a neutralizing agent in fermentation.

10. The process according to claim 1 or 4, wherein said recovery of said lactic acid from said lactic acid aqueous solution is effected by contacting said solution with a lactic acid extractant.

11. The process according to claim 1 or 4, wherein said recovery of said lactic acid from said aqueous solution is effected by contacting said solution with a lactic acid absorbent.

12. The process according to claim 1 or 4, wherein said recovery of said lactic acid from said aqueous solution is effected by contacting said solution with an anion exchanger in its free base form.

13. The process according to claim 12, wherein said anion exchanger is a water-immiscible liquid anion exchanger.

14. The process according to claim 12, wherein said anion exchanger is a solid anion exchanger.

15. The process according to claim 12, wherein said anion exchanger, in its free base form, has an apparent basicity corresponding to pKa of not higher than 6.

16. The process according to claim 12, wherein said anion exchanger, in its free base form, has an apparent basicity corresponding to pKa of not higher than 4.5.

17. The process according to claim 12, wherein said cation exchanger and said anion exchanger are simultaneously contacted with said lactate salt-containing aqueous solution.

18. The process according to claim 12, wherein said cation exchanger sand said anion exchanger are repeatedly alternately contacted with said lactate salt-containing aqueous solution.

19. The process according to claim 12, wherein said anion exchanger is separated from said lactate salt-containing aqueous solution by an anion exchange membrane.

20. The process according to claim 12, wherein said anion exchanger is separated from said lactate salt-containing aqueous solution by a dense neutral hydrophilic membrane.

21. The process according to claim 12, wherein said anion exchanger is separated form said lactate salt-containing aqueous solution by a dense neutral hydrophobic membrane.

22. The process according to claim 1 or 4, wherein said cation exchanger is separated from said lactate salt-containing aqueous solution by a cation exchange membrane.

23. The process according to claim 1 or 4, wherein said cation exchanger is separated form said lactate salt-containing aqueous solution by a dense neutral hydrophilic membrane.

24. The process according to claim 1 or 4, wherein said cation exchanger is separated from said lactate salt-containing aqueous solution by a dense neutral hydrophobic membrane.

25. The process according to claim 1 or 4, wherein said cation exchanger, in its free acid form, has an apparent acidity corresponding to a pKa of not lower than 2.

26. The process according to claim 1, wherein said regenerating in step (b) comprises a thermal hydrolysis to regenerate said cation exchanger in its acid form and to yield said second product.

27. The process according to claim 26, wherein said second product is selected from the group consisting of hydroxides, carbonates and bicarbonates of alkali and alkaline earth metals.

28. The process according to claim 3 or 4, wherein said heating is conducted at a temperature higher than 80° C.

29. The process according to claim 3 or 4, wherein said second product is transferred into a vapor phase.

30. The process according to claim 1 or 4, wherein said lactate salt is ammonium lactate and said second product is ammonia.

31. The process according to claim 1 or 4, wherein said lactate salt is a product of fermentation.

32. The process according to claim 1 or 4, wherein said contacting in step (a) is conducted in a $CO_2$-containing atmosphere.

* * * * *

UNITED STATES PATENT AND TRADEMARK OFFICE
CERTIFICATE OF CORRECTION

| | | |
|---|---|---|
| PATENT NO. | : 7,238,837 B1 | Page 1 of 1 |
| APPLICATION NO. | : 09/147914 | |
| DATED | : July 3, 2007 | |
| INVENTOR(S) | : Aharon Meir Eyal et al. | |

It is certified that error appears in the above-identified patent and that said Letters Patent is hereby corrected as shown below:

On title page, insert -- (73) Assignee: Cargill Incorporated, Wayzata, MN --.

Signed and Sealed this

Eighteenth Day of September, 2007

JON W. DUDAS
*Director of the United States Patent and Trademark Office*